US008643841B1

(12) United States Patent
Rotter et al.

(10) Patent No.: US 8,643,841 B1
(45) Date of Patent: Feb. 4, 2014

(54) ANGLE-RESOLVED SPECTROSCOPIC INSTRUMENT

(75) Inventors: Lawrence D. Rotter, Pleasanton, CA (US); David Y. Wang, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 317 days.

(21) Appl. No.: 13/028,245

(22) Filed: Feb. 16, 2011

(51) Int. Cl.
*G01J 4/00* (2006.01)
*G01J 3/28* (2006.01)

(52) U.S. Cl.
USPC .............................. 356/369; 356/326; 356/328

(58) Field of Classification Search
None
See application file for complete search history.

(56) References Cited

U.S. PATENT DOCUMENTS

| 5,412,473 | A | | 5/1995 | Rosencwaig et al. |
| 5,596,406 | A | | 1/1997 | Rosencwaig et al. |
| 5,880,834 | A | * | 3/1999 | Chrisp ........................ 356/328 |
| 2004/0184033 | A1 | * | 9/2004 | Nelson ........................ 356/302 |
| 2005/0174584 | A1 | * | 8/2005 | Chalmers et al. ............. 356/630 |
| 2005/0270524 | A1 | * | 12/2005 | Wang et al. .................... 356/326 |
| 2006/0268272 | A1 | * | 11/2006 | Liphardt et al. ............... 356/369 |

* cited by examiner

*Primary Examiner* — Gregory J Toatley
*Assistant Examiner* — Hina F Ayub
(74) *Attorney, Agent, or Firm* — Luedeka Neely Group, P.C.; Rick Barnes

(57) ABSTRACT

A method for optically inspecting a specimen by directing a probe beam onto the specimen at varying angle of incidence and azimuth angle, thereby producing a reflected probe beam, gathering the reflected probe beam, separating the reflected probe beam as a function of wavelength, adding astigmatism to separate the reflected probe beam as a function of at least one of the angle of incidence and the azimuth angle, and evaluating the specimen based at least on changes in the reflected probe beam as a function of wavelength of the reflected probe beam and at least one of the angle of incidence and the azimuth angle.

20 Claims, 3 Drawing Sheets

ANGLE-RESOLVED SPECTROSCOPIC INSTRUMENT

FIELD

This invention relates to the field of integrated circuit fabrication. More particularly, this invention relates to optical inspection and analysis, such as with spectroscopic ellipsometers and reflectometers.

INTRODUCTION

A basic ellipsometer includes an illumination source that creates a polychromatic probe beam. The probe beam is focused to create an illumination spot on the surface of a specimen. Polarizing optics impart a known polarization state to the probe beam. The reflected probe beam passes through analyzing optics, before being focused onto a detector. One or more of the polarizing and analyzing optics may be rotated. The detector converts the reflected probe beam into signals that are analyzed by a processor. If the detector is an array detector that is placed in a plane conjugate to the pupil plane of the objective, the system is a beam profile reflectometer or ellipsometer. Adding a slit on the collection side of the instrument allows simultaneous detection of light at multiple wavelengths as well as at multiple angles of incidence.

SUMMARY OF THE CLAIMS

Embodiments of the present invention include a method for optically inspecting a specimen by directing a probe beam onto the specimen at varying angle of incidence and azimuth angle, thereby producing a reflected probe beam, gathering the reflected probe beam, separating the reflected probe beam as a function of wavelength, adding astigmatism to separate the reflected probe beam as a function of at least one of the angle of incidence and the azimuth angle, and evaluating the specimen based at least on changes in the reflected probe beam as a function of wavelength of the reflected probe beam and at least one of the angle of incidence and the azimuth angle.

In this manner, embodiments according to the present invention simultaneously disperse wavelength and angle of incidence by substituting an astigmatic or other distortion element for the slit described in the introduction of this document, which reduces or eliminates the diffraction that is caused by the slit, and enables access to larger angles of incidence by working off-axis. Thus, ellipsometers according to the embodiments of the present invention simultaneously measure ellipsometric parameters over a range of wavelengths, incident angles, and azimuth angles by forming an astigmatic image of the measurement spot for each wavelength in the spectrum.

In various embodiments according to this aspect of the invention, the probe beam source directs the probe beam to the specimen off-axis. In other embodiments the angle of incidence is normal to the specimen. In some embodiments the probe beam source is a broadband source, and in other embodiments the probe beam source is a combination of a plurality of narrowband sources. In some embodiments changes in intensity of the probe beam are measured by the detector. In some embodiments changes in a polarization state of the probe beam are converted to changes in intensity of the probe beam by analyzing optics. Those changes in intensity of the probe beam are measured by the detector.

According to another aspect of the invention there is described an instrument for optically inspecting a specimen, the instrument having a probe beam source for directing a probe beam onto the specimen at varying angle of incidence and azimuth angle, thereby producing a reflected probe beam, first optics for separating the reflected probe beam as a function of wavelength, an astigmatic element for separating the reflected probe beam as a function of at least one of the angle of incidence and the azimuth angle, a detector for receiving the reflected probe beam, and a processor for evaluating the specimen based at least on changes in the reflected probe beam as a function of wavelength of the reflected probe beam and at least one of the angle of incidence and the azimuth angle.

According to yet another aspect of the invention there is described an instrument for optically inspecting a specimen of the type having a probe beam source for directing a probe beam onto the specimen at varying angle of incidence and azimuth angle and thereby producing a reflected probe beam, first optics for separating the reflected probe beam as a function of wavelength, and a detector for receiving the reflected probe beam, and including an astigmatic element for separating the reflected probe beam as a function of at least one of the angle of incidence and the azimuth angle before the reflected probe beam attains the detector, and a processor for evaluating the specimen based at least on changes in the reflected probe beam as a function of wavelength of the reflected probe beam and at least one of the angle of incidence and the azimuth angle.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
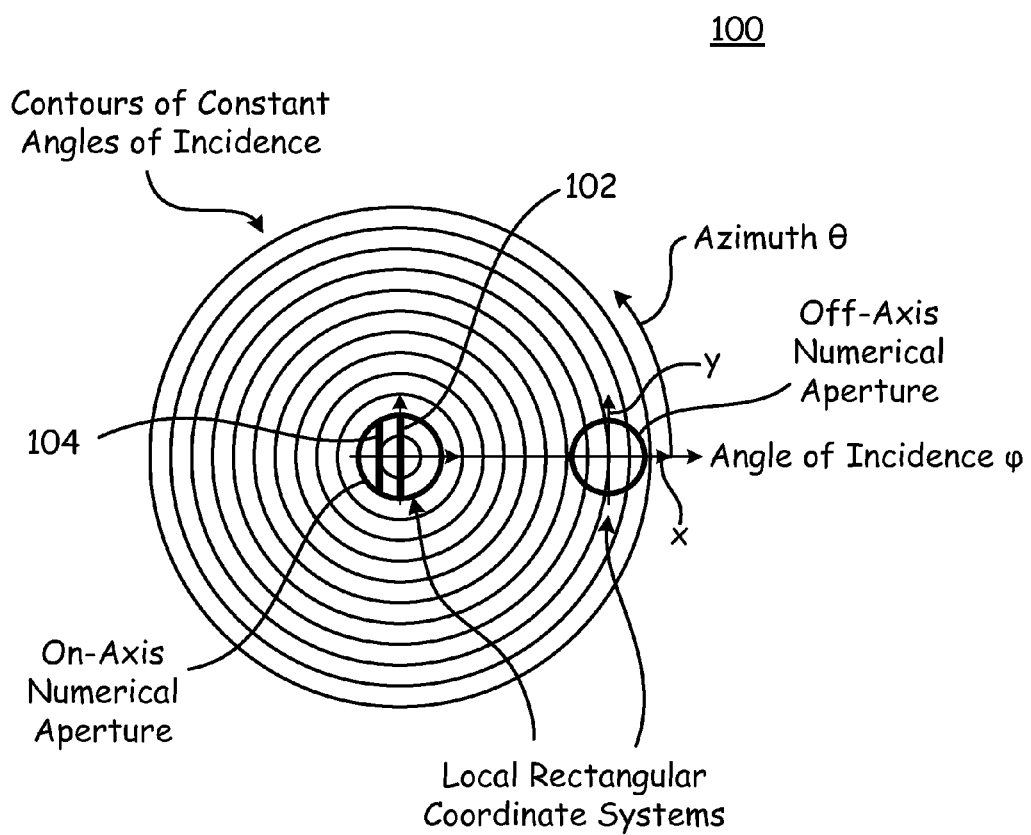
FIG. 1 depicts the angle of incidence and azimuth angle contours for an instrument according to an embodiment of the present invention.

Embodiments of spectrometers of the present invention cover both on-axis and off-axis ellipsometers and broadband reflectometers. Whereas ellipsometers measure changes in the polarization state of light, reflectometers measure changes in the intensity of light.

In some embodiments where the measurement spot on the specimen is determined by the illumination side optics, the astigmatism is selectively applied between the specimen and the entrance slit of the spectrograph. A non-astigmatic spectrograph then forms an astigmatic image of the measurement spot for each wavelength in the spectrum. In some embodiments where monochromatic light is passed through the instrument, such as by using a monochromator with a broadband light source, the detector is moved directly to the astigmatic image plane.

While various different embodiments are contemplated herein, the following discussion provides a detailed description of an embodiment where the instrument includes an astigmatic spectrograph.

In the presence of astigmatism, the image of the measurement spot forms two lines, generally referred to as sagittal and tangential line foci. Between the astigmatic focal planes, the image appears as a circular or elliptical blur. In some embodiments, the detector plane is placed at or near either one of the sagittal or tangential focal plane.

The angle of incidence or azimuth angle at the specimen is calculated by adding the axial ray incidence angle to the marginal ray height divided by the focal length of the illumination optics. Astigmatism varies linearly with marginal ray height. Specimen properties at different angles of incidence or azimuth angles can be extracted by sampling the detector signals at different points along the astigmatic image.

In some embodiments the detector is a two-dimensional array of detector elements, such as a two dimensional charge-coupled device array, and is oriented such that one of the columns or rows of the detector array elements are perpendicular to the direction of wavelength dispersion, and the other of the rows or columns of the detector array elements are perpendicular to the direction of the astigmatic image containing angle of incidence or azimuth angle information.

In some embodiments the astigmatic image is sized to sample the desired angle of incidence or azimuth angle range in the direction perpendicular to the wavelength dispersion. In some of these embodiments the astigmatic image is no larger than the width of the active area of the detector, in the direction perpendicular to wavelength dispersion. In some embodiments the astigmatic image size is no larger than the spatial resolution of the spectrograph in the direction of wavelength dispersion, so as to make use of as much of the spectral resolution of the spectrograph as possible.

The astigmatic image is generated by one or more optical elements that introduce astigmatism. Such optical elements include cylindrical lenses, cylindrical mirrors, off-axis spherical minors, and spherical holographic gratings that are oriented off of the non-astigmatic deviation angle.

The detector signal is downloaded into a two-dimensional data array I having columns i and rows j. I(i,j) from a single detector element is the signal $I(\lambda_i, \phi_j)$ at a particular wavelength $\lambda_i$ and angle of incidence $\phi_j$. Embodiments of the present invention measure:

$$I(\lambda,\phi)=\int_{\theta_{min}}^{\theta_{max}} I(\lambda,\phi,\theta)d\theta, \quad \text{Equation 1}$$

where $\theta$ is the azimuth angle. The advantage of measuring $I(\lambda, \phi)$ over measuring only $I(\lambda)$, such as by:

$$I(\lambda)=\int_{\theta_{min}}^{\theta_{max}}\int_{\phi_{min}}^{\phi_{max}} I(\lambda,\phi,\theta)d\phi d\theta \quad \text{Equation 2}$$

is that $I(\lambda, \phi)$ contains more information than $I(\lambda)$, because information is always lost in an averaging process. For example, sharp features in $I(\lambda, \phi)$ are broader in $I(\lambda)$, minima points in $I(\lambda, \phi)$ are higher in $I(\lambda)$, and maxima points in $I(\lambda, \phi)$ are lower in $I(\lambda)$. The larger the integration range of the angle of incidence, the more information that is lost. Because more data is available in $I(\lambda, \phi)$, a more sensitive determination of the properties of the specimen—such as layer thicknesses, optical constants, and critical dimensions—can be made.

However, equation 1 represents an averaging over azimuth angles that also loses some amount of information. To deal with cases where there is useful information in azimuth angle—critical dimension structures for example—$\theta$ and $\phi$ can be swapped in equation 1 so that the detector provides an array of data as a function of both wavelength and azimuth angle—$I(\lambda_i, \phi_j)$. Using a beam splitter to send beams to two separate spectrographs permits both $I(\lambda_i, \phi_j)$ and $I(\lambda_i, \theta_j)$ to be collected simultaneously.

The contours of constant angle of incidence in the pupil plane are circular arcs that are roughly parallel to the specimen, as depicted by representation 100 in FIG. 1. To the extent that the pupil plane can be approximated by a section of a sphere centered on the measurement point, the contours of constant angle of incidence are latitudes, and the contours of constant azimuth angle are longitudes. Ideally, the distortion in the spectrograph straightens those contours into lines at the detector array. Such is the case described above. Alternately there is some angle of incidence mixing, as given by:

$$I(\lambda,\phi_j)=\int I(\lambda,\phi)g(\phi,\phi_j)d\phi \quad \text{Equation 3}$$

where $g(\phi, \phi_j)$ is a family of angle of incidence distribution functions about $(\phi_j)$. For typical values of numerical aperture, $g(\phi, \phi_j)$ is relatively narrow in comparison to $\phi_{max}$ minus $\phi_{min}$, so there is still a gain in sensitivity from reduced angle averaging. Equation 3 similarly applies to the azimuth angle by substituting $\theta$ for $\phi$.

In reality, representation 100 is wrapped around a hemisphere that is centered on the measurement spot, but all of the essential features are more easily illustrated in a planar depiction. One feature is that angle of incidence and azimuth angles are the radial and angular coordinates, respectively, of a global cylindrical coordinate system. Concentrating first on the circle representing the numerical aperture of an off-axis ellipsometer, the local rectangular coordinate system approximates the cylindrical coordinate system near the origin of the local rectangular coordinate system. The local x-coordinate mainly maps angle of incidence, while the local y-coordinate mainly maps azimuth angle.

In the prior art, the spectrograph collapsed the numerical aperture circle to a point. However, the line foci of astigmatic spectrographs according to the present invention collapse the numerical aperture circle onto one or the other of the local rectangular coordinates. Therefore, the line focus that collapses the numerical aperture circle to the local x-axis maintains most of the angle of incidence information, while averaging over the azimuth angle, as given by equations 1 and 2. Similarly, the line focus that collapses the numerical aperture circle to the local y-axis maintains most of the azimuth information, while averaging over angle of incidence.

The situation is different for the on-axis case. A local rectangular coordinate system cannot approximate the cylindrical coordinate system near the global origin. As a result, the angle of incidence or azimuth angle distribution function g as given in equation 3 is not as narrow as in the off-axis case. However, there is still some advantage in using the astigmatic spectrograph, because not all of the distribution functions are as broad as in the prior art. For example, when region 102 of FIG. 1 is collapsed to the x-axis by astigmatic focusing, the entire range of angle of incidence in the numerical aperture is averaged together, as in the prior art. Region 104, however, spans a smaller range of angle of incidence. Therefore, some angle of incidence information is retained. Region 102, however, represents a single azimuth angle. By using an optical element, such as a Dove prism, to rotate the pupil plane relative to the astigmatic image plane, the spectrum versus the azimuth angle can be mapped out as $I(\lambda, \theta)$.

Figure 2:
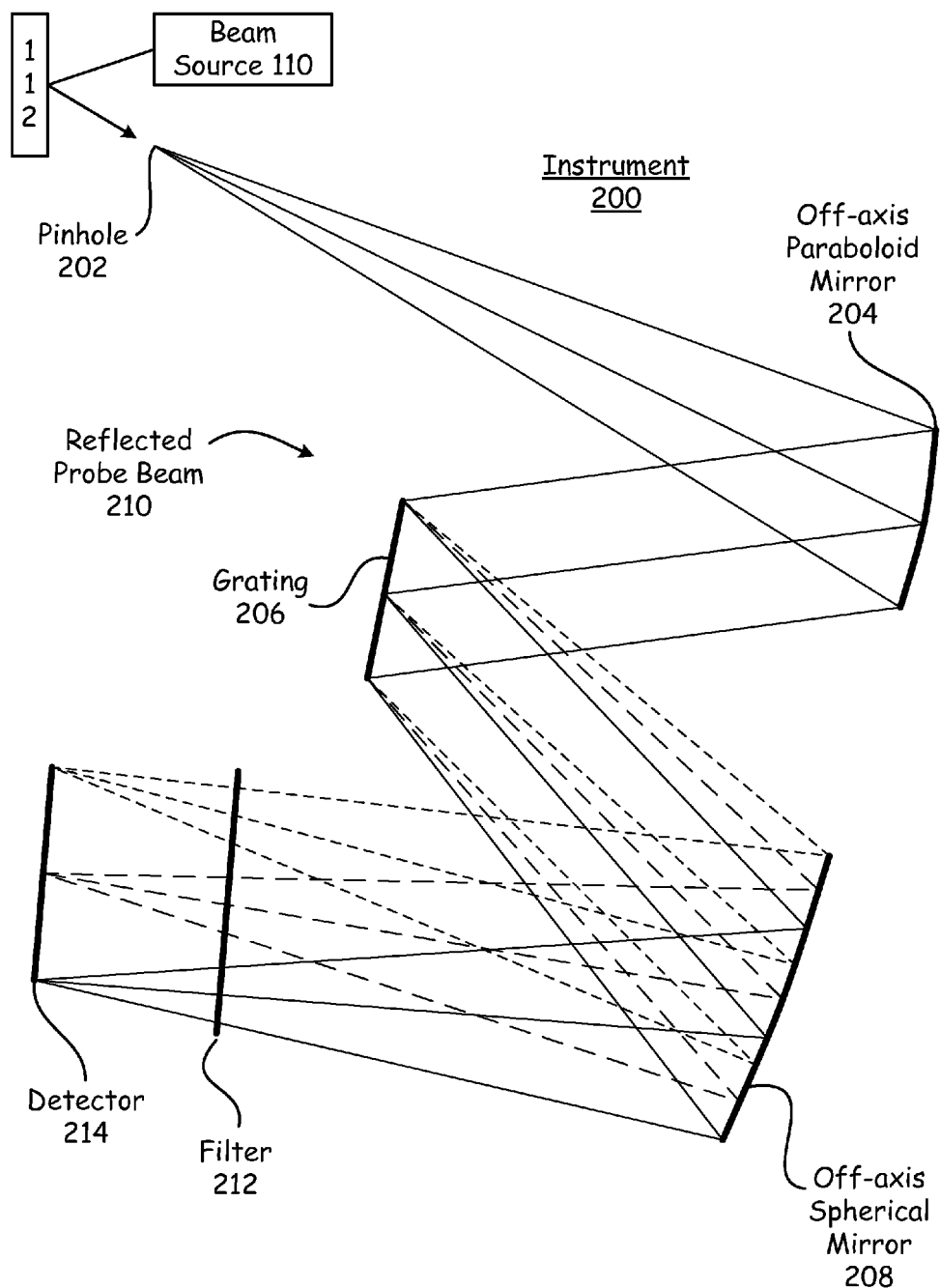
FIG. 2 depicts an instrument 200 according to an embodiment of the present invention, and most especially the reflected light path.

FIG. 2 depicts one embodiment of the angle-resolved spectroscopic instrument 200 according to the present invention. A set of collection-side optics gathers a reflected probe beam 210 through a pinhole 202. The gathered probe beam 210 is collimated by an off-axis paraboloid minor 204 or other suitable minor or lens. The collimated illumination 210 is forwarded to a grating 206 where it is dispersed into a spectrum. A prism or other optical device may be used in place of the grating 206. The illumination 210 is then forwarded to an astigmatism-generating optical element 208, such as an off-axis spherical minor. The illumination 210 is then forwarded to an order sorting filter 212 and onto a detector 214. The detector 214 in one embodiment is a two-dimensional array. The illumination 210 is spread spectrally along the length of the detector 214 as depicted in FIG. 2. The illumination 210 is distributed as a function of angle of incidence in a direction that is generally perpendicular to the plane of the paper on which the detector 214 is depicted in FIG. 2.

In some embodiments the beam source 110 of the light 210 is one or more broad band lamps, but in other embodiments is a combination of narrow band sources, such as lasers, which direct a probe beam toward the specimen 112. It is appreciated that the off-axis spherical mirror 208 is representative and that any spectrometer optic that generates astigmatism in a plane conjugate to the specimen can be used, as mentioned above.

Figure 3A:
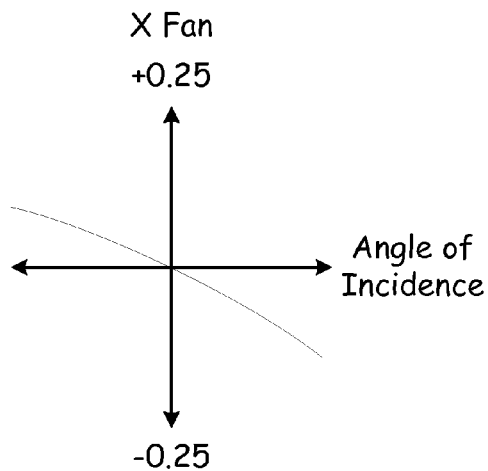
FIGS. 3 and 4 are graphs of relative field height depicting X fan ray and Y fan ray departure relative to the axial ray due to an astigmatic element according to an embodiment of the present invention.
Figure 3B:
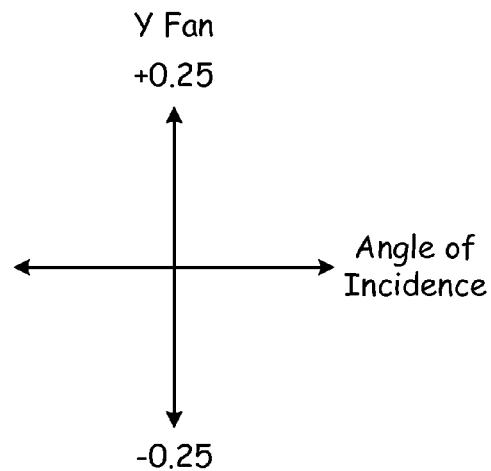

FIGS. 3A and 3B depict a ray aberration plot for one embodiment of the astigmatic element of the instrument 200, such as the minor 208, where the x axis represents the normalized entrance pupil size, corresponding to the angle of incidence at the specimen. The y-axis in FIG. 3A is the X-fan ray departure relative to the axial ray. The y-axis In FIG. 3B is the Y-fan ray departure relative to the axial ray. It is appreciated that the astigmatism is limited to one axis (in this case the X fan), as depicted.

Figure 4A:
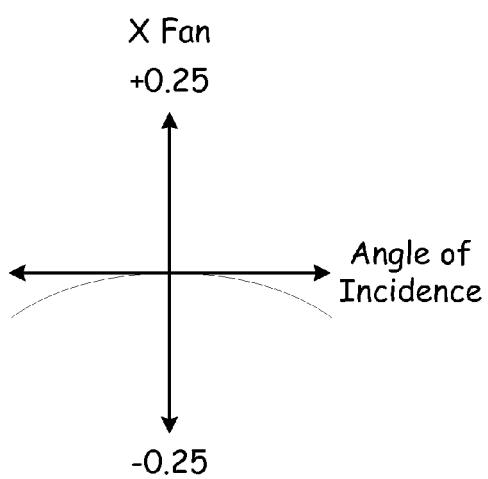
Figure 4B:
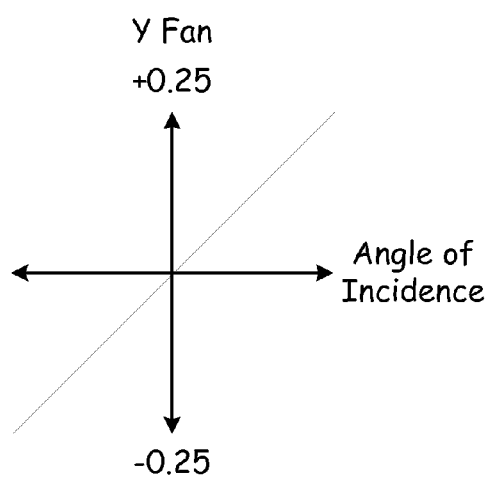

FIGS. 4A and 4B shows a ray aberration plot for another embodiment of the astigmatic element of the instrument 200. As depicted in FIG. 4A, the angle of incidence (on the X axis) has only a limited impact on the Y location of a ray that is received at the detector. In contrast, as shown in FIG. 4B, the angle of incidence (on the X axis) has an almost direct relation to the X location of the ray that is received at the detector (or pixel blurring). The limited dependence between angle of incidence and Y location may be reduced or eliminated by signal processing performed after detection.

The astigmatism may be included in the diffracting element 206, as in a spherical holographic grating used at a deviation angle that produces point-to-line imaging instead of the usual point-to-point imaging. In this case, the off-axis paraboloid 204 and spherical minor 208 of FIG. 2 are absent. The spectrograph 200 consists of a pinhole 202, a point-to-line imaging diffraction grating 206, optionally an order-sorting filter 212, and a detector 214.

In summary, measuring at least one of $I(\lambda, \phi)$ and $I(\lambda, \theta)$ permits the optimization of certain design parameters. For example, the angle of incidence range may overlap Brewster's angle, $\phi_B$. This troublesome singularity at $\phi_B$ may be dealt with easily by eliminating the row (or column) of data $I(\lambda, \phi_B)$. The remaining data $I(\lambda, \phi_i)$ have high sensitivity because the $\phi_i$ are near $\phi_B$. The system numerical aperture may be increased without loss of sensitivity. A larger numerical aperture results in accurate measurements on smaller measurement spots. When measuring $I(\lambda)$ the larger numerical aperture results in integrating over a larger range of angles of incidence, which reduces sensitivity. When measuring $I(\lambda, \phi)$ the larger numerical aperture provides data over a larger range of angles of incidence, which increases sensitivity.

Nonuniformity of the intensity profile along the direction of angle of incidence or azimuth angle in the pupil plane can be normalized in the proposed instrument 200. In a typical instrument a particular profile must be assumed if the variation of angle of incidence or azimuth angle in the pupil plane is to be included in the calculation of the specimen properties. Utilizing the measured intensity profile improves tool matching. Measuring the azimuth angle profile $I(\lambda, \theta)$ simplifies determination of the mean azimuth angle, thereby improving critical dimension tool matching.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for optically inspecting a specimen, the method comprising the steps of:
   directing a probe beam onto the specimen at varying angle of incidence and azimuth angle, thereby producing a reflected probe beam,
   gathering the reflected probe beam,
   separating the reflected probe beam as a function of wavelength,
   adding astigmatism to separate the reflected probe beam as a function of at least one of the angle of incidence and the azimuth angle, and
   evaluating the specimen based at least on changes in the reflected probe beam as a function of wavelength of the reflected probe beam and at least one of the angle of incidence and the azimuth angle.

2. The method of claim 1 wherein the angle of incidence is normal to the specimen.

3. The method of claim 1 wherein the probe beam is directed to the specimen off-axis.

4. The method of claim 1 wherein the probe beam is generated from a broadband source.

5. The method of claim 1 wherein the probe beam is generated by a combination of a plurality of narrowband sources.

6. The method of claim 1 wherein changes in intensity of the probe beam are measured.

7. The method of claim 1 wherein changes in a polarization state of the probe beam are measured.

8. An instrument for optically inspecting a specimen, the instrument comprising:
   a probe beam source for directing a probe beam onto the specimen at varying angle of incidence and azimuth angle, thereby producing a reflected probe beam,
   first optics for separating the reflected probe beam as a function of wavelength,
   an astigmatic element for separating the reflected probe beam as a function of at least one of the angle of incidence and the azimuth angle,
   a detector for receiving the reflected probe beam, and
   a processor for evaluating the specimen based at least on changes in the reflected probe beam as a function of wavelength of the reflected probe beam and at least one of the angle of incidence and the azimuth angle.

9. The instrument of claim 8 wherein the angle of incidence is normal to the specimen.

10. The instrument of claim 8 wherein the probe beam source directs the probe beam to the specimen off-axis.

11. The instrument of claim 8 wherein the probe beam source is a broadband source.

12. The instrument of claim 8 wherein the probe beam source is a combination of a plurality of narrowband sources.

13. The instrument of claim 8 wherein changes in intensity of the probe beam are measured by the detector.

14. The instrument of claim 8 wherein changes in a polarization state of the probe beam are measured by the detector.

15. In an instrument for optically inspecting a specimen of the type having a probe beam source for directing a probe beam onto the specimen at varying angle of incidence and azimuth angle and thereby producing a reflected probe beam, first optics for separating the reflected probe beam as a function of wavelength, and a detector for receiving the reflected probe beam, the improvement comprising:
- an astigmatic element for separating the reflected probe beam as a function of at least one of the angle of incidence and the azimuth angle before the reflected probe beam attains the detector, and
- a processor for evaluating the specimen based at least on changes in the reflected probe beam as a function of wavelength of the reflected probe beam and at least one of the angle of incidence and the azimuth angle.

16. The instrument of claim 15 wherein the probe beam source directs the probe beam to the specimen off-axis.

17. The instrument of claim 15 wherein the probe beam source is a broadband source.

18. The instrument of claim 15 wherein the probe beam source is a combination of a plurality of narrowband sources.

19. The instrument of claim 15 wherein changes in intensity of the probe beam are measured by the detector.

20. The instrument of claim 15 wherein changes in a polarization state of the probe beam are measured by the detector.

* * * * *